United States Patent [19]
Singh et al.

[11] Patent Number: 5,811,437
[45] Date of Patent: Sep. 22, 1998

[54] METHODS OF INCREASING NITRIC OXIDE SYNTHESIS

[75] Inventors: Jai Pal Singh, Carmel; Danny Lee Wood, Indianapolis, both of Ind.

[73] Assignee: Eli Lilly and Company, Indianapolis, Ind.

[21] Appl. No.: 840,528

[22] Filed: Apr. 22, 1997

Related U.S. Application Data

[60] Provisional application No. 60/018,071 May 21, 1996.

[51] Int. Cl.$^6$ ................................................. A61K 31/445
[52] U.S. Cl. .......................................................... 514/324
[58] Field of Search ............................................. 514/324

[56] References Cited

U.S. PATENT DOCUMENTS

| | | | |
|---|---|---|---|
| 4,418,068 | 11/1983 | Jones . | |
| 5,393,763 | 2/1995 | Black et al. | 514/333 |
| 5,447,941 | 9/1995 | Zuckerman | 514/324 |
| 5,457,113 | 10/1995 | Cullinan et al. . | |
| 5,462,937 | 10/1995 | Cullinan et al. . | |
| 5,464,845 | 11/1995 | Black et al. . | |
| 5,485,827 | 1/1996 | Zapol et al. | 128/200.14 |
| 5,622,975 | 4/1997 | Singh et al. . | |

OTHER PUBLICATIONS

Herrington, et al., *American Journal of Card.*, 73, pp. 951–952 (1994).
Williams, et al., *Circulation*, 81(5), pp. 1680–1687 (1990).
Weiner, et al., *Proc. Natl. Acad. Sci.*, 91, pp. 5212–5216 (1994).
Hayashi, et al., *Biochemical &Biophysical Res. Comm.*, 203(2), pp. 1013–1019 (1994).
Upchurch, et al., *J. Nutr.*, 126, pp. 1290S–1294S (1996).
Higman, et al., *Arteriosclerosis, Thrombosis, &Vascular Biology*, 16(4), pp. 546–552 (1996).
Vallance, et al., *Journal of the Royal College of Physicians of London*, 28(3), pp. 209–219 (1994).
Cayatte, et al., *Arteriosclerosis and Thrombosis*, 14(5), pp. 753–759 (1994).
Joannides, et al., *Circulation*, 91(5) pp. 1314–1319 (1995).
Clarkson, et al.,*J. Clin. Invest.*, 97(8) pp. 1989–1994 (1996).
Petrie, et al., *Circulation*, 93(7), pp. 1331–1333 (1996).
Scherrer, et al., *J. Clin. Invest.*, 94, pp. 2511–2515 (1994).
Moncada, et al., *New England Journal of Medicine*, 329(27), pp. 2002–2012 (1993).

*Primary Examiner*—Raymond Henley, III
*Attorney, Agent, or Firm*—James J. Sales; David E. Boone

[57] ABSTRACT

The current invention provides methods for increasing the concentration of nitric oxide (NO) in vascular endothelial cells, comprising administering a compound of formula I

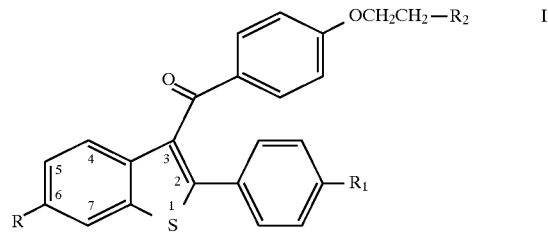

Wherein:

R is hydrogen, —OH, —O($C_1$–$C_4$ alkyl), —OCO($C_1$–$C_4$ alkyl), or —OCOAr where Ar is a phenyl or optionally substituted phenyl;

$R_1$ is R, —$C_1$, or —F;

$R_2$ is 1-pyrrolidinyl, 1-piperidinyl, or 1-hexamethyleneimino;

or a pharmaceutically acceptable salt or solvate thereof.

4 Claims, No Drawings

METHODS OF INCREASING NITRIC OXIDE SYNTHESIS

This application claims the benefit of U.S. Provisional Application 60/018,071, filed May 21, 1996.

FIELD OF THE INVENTION

The present invention deals with the fields of organic chemistry and pharmacology and provides for compounds and methods for increasing the synthesis of endothelial nitric oxide (NO), particularly in vascular endothelial cells.

BACKGROUND OF THE INVENTION

Nitric oxide is a regulatory molecule that plays a vital role in the normal physiology of the cardiovascular, intestinal, central nervous, and immune systems. Nitric oxide is synthesized from L-arginine by a family of enzymes known as NO synthase (NOS). Particularly germane to the present invention is the calcium dependent NOS produced in the vascular endothelial cells, known as eNOS. Recently, there have been numerous studies which have linked the regulation of the eNOS gene with the hormone estrogen. Estrogen has been shown to up-regulate the production of eNOS m-RNA and consequently, the synthesis of eNOS in endothelial cells. This increase in the amount of eNOS allows the endothelial cells produce more NO in response to the appropriate stimuli in the vascular system.

In the vasculature, endothelial derived NO has several actions among which are the inhibition of platelet aggregation, adhesion of inflammatory cells, and the proliferation of smooth muscle cells. Endothelial derived NO is an important regulator of vascular tone. Flow dependent dilation, a commonly used index of endothelial functions, is largely mediated by NO.

The mechanism for the regulation of vascular tone by NO is initiated by stimuli, such as acetylcholine, bradykinin, shear stress, etc., on the endothelial, lining cells. The endothelial cells respond by producing NO from L-arginine by eNOS. The NO produced leaves the endothetial cells and stimulates the activity guanylate cyclase in the adjoining smooth muscle cells. Activation of guanylate cyclase increases the level of cGMP and causes the smooth cell to relax, thus dilating the vessel and increasing the blood flow. For further information, see: Moncada et al., *New Eng. J. Med.*, 329, pp. 2002–2012 (1993), and Vallance, et al., *J. Royl. Coll. Physician London*, 28, pp. 209–219 (1994).

Reduced endothelial NO generation may lead to impaired vasodilatation, abnormal vasospasm, increased platelet aggregation, and increased adhesion and infiltration of inflammatory cells. Impairment of endothelial NO and endothelial function are associated with the risk factors for coronary artery disease including smoking, hypercholesterolemia, homocycteinuria, and diabetes. Alteration of NO modulated activities in the coronary arteries may contribute to acute coronary syndrome leading to myocardial infarction. Impairment of the endothelial NO system and its resulting vasoconstriction have been implicated in exacerbating the damage to neurons in cerebral ischemic events, such as, stroke. Additionally, recent studies indicate that endothelial NO mediates the vascular sensitivity to insulin, thus enhanced NO production may be useful in treating the vascular effects of diabetes.

In general, there is a large body of evidence, both experimental and clinical, which indicates increasing the levels of NO in the vasculature is beneficial in many pathologic conditions, such as diabetes, stroke, atherosclerosis, and hypertension.

Current therapy to enhance NO levels in the vasculature has been either to administer high doses of L-arginine (the eNOS substrate) or compounds such as nitroglycerine or sodium nitroprusside, which metabolically release NO. Although, these therapies can be effective, each has shown undesirable side-effects. Additionally, these therapies suffer from their inability to maintain a sustained release of NO, due to their rapid clearance from the body.

It would be of great benefit if a new therapy were available to increase concentrations of NO in the vasculature.

SUMMARY OF THE INVENTION

The current invention provides methods for increasing endothelial derived NO comprising administering to a human in need thereof an effective amount of a compound of formula I

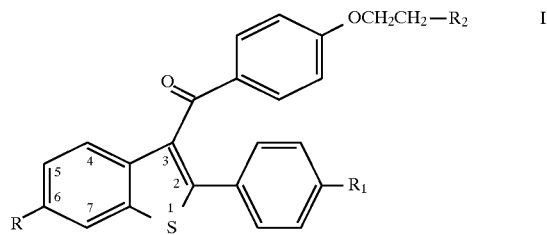

Wherein:

R is hydrogen, —OH, —O($C_1$–$C_4$ alkyl), —OCO($C_1$–$C_4$ alkyl), or —OCOAr where Ar is a phenyl or optionally substituted phenyl;

$R_1$ is R, —Cl, or —F;

$R_2$ is 1-pyrrolidinyl, 1-piperidinyl, or 1-hexamethyleneimino;

or a pharmaceutically acceptable salt or solvate thereof.

DETAILED DESCRIPTION OF THE INVENTION

The current invention is related to the discovery that a select group of 2-aryl benzo[b]thiophenes, the compounds of formula I, are useful for increasing eNOS and endothelial derived NO concentration.

General terms used in the description of compounds herein described bear their usual meanings. For example, "$C_1$–$C_4$ alkyl" refers to straight or branched aliphatic chains of 1 to 4 carbon atoms including methyl, ethyl, propyl, iso-propyl, n-butyl, and the like.

The term "substituted phenyl" refers to a phenyl group having one or two substituents selected from the group consisting of $C_1$–$C_4$ alkyl, $C_1$–$C_4$ alkoxy, hydroxy, nitro, chloro, fluoro, or tri(chloro or fluoro)methyl. "O($C_1$–$C_4$ alkyl)" refers to a $C_1$–$C_4$ alkyl group attached through an oxygen bridge such as methoxy, ethoxy, n-propoxy, iso-propoxy, and the like.

The term, "pharmaceutically acceptable salt" refers to either acid or base addition salts which are known to be non-toxic and are commonly used in the pharmaceutical literature. Commonly used acid addition salts include: inorganic salts formed by the addition of sulfuric acid, nitric acid, hydrochloric acid, hydrobromic acid phosphoric acid, phosphorous acid and the like; or organic salts formed by the addition of acetic acid, formic acid, benzoic acid, citric acid, methanesulfonic acid and the like. Commonly used basic addition salts would include salts formed by alkali or alkaline earth hydroxides, ammonium hydroxide, alkyl or aromatic amines and the like. A preferred salt of this invention would be the hydrochloride salt.

The phrase "inhibiting a physiological condition associated with a lack of or need for nitric oxide (NO)" includes prohibiting, preventing, restraining, and slowing, stopping, or reversing progression, severity or a resultant symptom or effect of said physiological condition. Such physiological conditions include those mentioned in this application, such as pathological platelet aggregation, pathological vasoconstriction, vascular effects of diabetes, stroke, atherosclerosis, and abnormal vasospasm.

The term "solvate" represents an aggregate that comprises one or more molecules of a solute, such as a formula I compound, with one or more molecules of a suitable solvent.

Raloxifene hydrochloride, which is a preferred embodiment of this invention, is a compound of formula I, where R and $R_1$ each are hydroxyl; $R_2$ is 1-piperidinyl; and it is as its hydrochloride salt. Raloxifene is named: [2-(4-hydroxyphenyl)-6-hydroxybenzo[b]thien-3-yl][4-[2-(1-piperidenyl)ethoxy]phenyl]methanone hydrochloride.

Generally, at least one compound of formula I is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, 4,380,635, and 5,393,763, all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

As used herein, the term "effective amount" means an amount of compound of formula I which is capable of increasing endothelial derived NO concentration in a human in need of such treatment. Humans in need of treatment would include, but not be limited to, those suffering from vasoconstriction or inappropriate platelet aggregation due to impairment of the endothelial NO regulatory pathway by coronary disease risk factors, diabetes, and the like. As envisioned in this invention, a compound of formula I would be useful in inhibiting, ameliorating, reducing, limiting, or preventing pathological sequelae due to impairment of the endothelial NO regulatory pathway.

The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 0.1 mg to about 1000 mg/day of a compound of the present invention, and more particularly will be from about 15 mg to about 80 mg/day from once to three times each day or as often as needed for efficacy.

In addition, compounds of formula I may be used concurrently or sequentially with other agents which interact with the endothelial NO pathway, e.g., nitroglycerin, sodium nitroprusside, L-arginine, and the like.

By "pharmaceutically acceptable formulation" it is meant that the carrier, diluent, excipients and salt must be compatible with the active ingredient (a compound of formula I) of the formulation, and not be deleterious to the recipient thereof.

Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The formulations which follow are given for purposes of illustration and are not intended to be limiting in any way. The total active ingredients in such formulations comprises from 0.1% to 99.9% by weight of the formulation. The term, "active ingredient" means a compound of formula I or a salt or solvate thereof.

FORMULATIONS

Formulation 1:
Gelatin Capsules
Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules. The formulation above may be changed in compliance with the reasonable variations provided.

A tablet formulation is prepared using the ingredients below:

Formulation 2:
Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3:
Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4:
Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5:
Aerosol

| Ingredient | Quantity (% by weight) |
| --- | --- |
| Active ingredient | 0.25 |
| Ethanol | 25.75 |
| Propellant 22 | 70.00 |
| (Chlorodifluoromethane) | |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6:
Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7:
Intravenous Solution

| Ingredient | Quantity |
| --- | --- |
| Active ingredient | 50 mg |
| Isotonic saline | 1,000 mL |

The solution of the above ingredients is intravenously administered to a patient at a rate of about 1 mL per minute.

TEST PROCEDURE

As evidence of the utility of the compounds of the current invention to elevate the concentration of NO in endothelial tissue, the following test system was used.

Cell Cutures

Cryopreserved single donor human umbilical vein endothelial cells (HUVEC) were purchased from Clonetics Corporation, San Diego Ca. These cells are defined by Clonetics to be 1° (first passage cells). The cells are stored in liquid nitrogen and aliquots taken fresh for each experiment. The cells are thawed and placed into a T-75 flask with 75 mL of media. For all HUVEC cultures, all labware (Corning) was coated with 0.2% gelatin (Sigma Chemical Co.) in M199 media (Gibco) for twenty minutes at 37° C. Cells were grown in phenol red free M199, with 10% fetal bovine serum (Gibco), 50 ug/mL of endothelial cell growth supplement(Collaborative Biochemical Products, Bedford Mass.), 100 ug/mL of porcine heparin (Gibco), 10 units/mL of penicillin, 10 ug/mL of streptomycin, and 0.2 mM of L-glutamine at 37° C. and 5% $CO_2$. When the 2° culture cells reach 70–90% confluence, they are split 1:3 onto gelatin coated T-75 flasks with 15 mL of media to produce 3° culture cells. After these cultures have reached 70–90% confluence, typically 3–4 days, these 4° culture cells were split onto 1:3 onto coated 12 well plates in 1 mL of media. All experiments were conducted with these fourth passage cells. After 72 hours, the cells were confluent and the drug treatments were initiated. The old media was aspirated off and 1 mL of drug testing media with the drug was added (15% gelded horse serum (Gemini Bioproducts, Calabasas Calif., 10 units/mL of penicillin, 10 ug/mL of streptomycin, and 0.2 mM of L-glutamine). Stock solutions of the test compounds of formula I or 17-β-estradiol were prepared at 10 mM in DMSO. The cells were treated with the drug for 48 hours at 37° C.

Induction of Nitric Oxide Dependent cGMP

Three plates (one experimental) are taken out of the incubator and placed on a paper towel to prevent cooling. One plate at a time, media is removed, and 1 mL of warm HBSS (Gibco) is added. This is removed and replaced with 0.5 mL of equilibration buffer ±200 uL of L-NAME (N-nitro-L-arginine methyl ester, Sigma). The equilibration buffer consists of HBSS, 10 mM HEPES, 1.2 mM $CaCl_2$, 0.6 mM $MgSO_4$, and 0.5 mM isobutyl methyl xanthine(IBMX) and 10 uM L-arginine, which are added fresh to each stock solution. The IBMX is made as a 200 mM stock solution in DMSO at 37° C. The cells are allowed to equilibrate for 30 minutes at 37° C. in 5% $CO_2$. After the incubation, 0.5 mL of "stimulation" buffer with stimulant is added for 10 minutes. Stimulation buffer for the controls consists of the equilibration buffer plus a designated stimulant, which are: 1) negative control, 2) positive control, 1 mM sodium nitroprusside (Sigma), 3) 1 uM of A-23187 (Calcium ionophore) (Sigma), 4) 1 uM of A-23187 and 200 uM of L-NAME (This control group demonstrates that the effects seen (cGMP increase) in this assay are due solely to the NO produced in the endothelial cells.) The test cells treated with the compounds of formula I are stimulated with 1 uM of A-23187. After 10 minutes, the buffers are removed and 200 uL of 0.01N HCl is added, and the cGMP is extracted by rocking the cells for 30 minutes at 4° C. Each 200 uL aliquot is placed in a tube containing 2 uL of 1N NaOH. The samples are frozen −20° C. for storage. To each well of the plate is added 250 uL of 0.5% SDS in 0.1N NaOH, to soublize the attached cells. Plates were wrapped in plastic wrap and frozen at −20° C. for later protein assay by the BCA method (Pierce Chemical Co.). (The average total amount of protein in mg was determined for all wells in an experiment and used to normalize the cGMP content.) cGMP cotent was determined by enzyme immunoassay (Amersham Co, RPN.226) as per the manufactures instructions for the acetylation protocol. Assays are done as per instructions except that acetylation of 200 uL samples was with 20 uL of reagent instead of the 100 uL for 1 mL samples. Assays were quantitied on a thermomax spectrophotometer at 450 nM.

The positive control of 17-β-estradiol demonstrated the expected increase in amount of NO dependent cGMP. The compounds of formula I were discovered to increase the concentration of NO and induce cGMP in these endothelial cells. In Table 1, the increase in NO dependent cGMP for raloxifene hydrochloride is shown.

TABLE 1

| Compound | Concentration[a] | cGMP Level[b] |
| --- | --- | --- |
| Control | — | 1.30 |
| Raloxifene | 0.1 | 2.55* |
|  | 1.0 | 2.65* |

[a]pM/mL
[b]pM/mg of protein
*p > .01

We claim:

1. A method for increasing nitric oxide (NO) synthesis in vascular endothelial cells in a human in need thereof, comprising administering to said human a compound of formula I

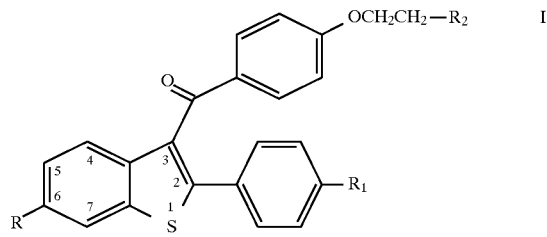

Wherein:
R is hydrogen, —OH, —O($C_1$–$C_4$ alkyl), —OCO($C_1$–$C_4$ alkyl), or —OCOAr where Ar is a phenyl or optionally substituted phenyl;
$R_1$ is R, —Cl, or —F;
$R_2$ is 1-pyrrolidinyl, 1-piperidinyl, or 1-hexamethyleneimino;
or a pharmaceutically acceptable salt or solvate thereof.

2. A method according to claim 1 wherein said compound of formula I is [2-(4-hydroxyphenyl)-6-hydroxybenzo[b]thien-3-yl][4-[2-(1-piperidinyl)ethoxy]phenyl]methanone hydrochloride.

3. A method for inhibiting a physiological condition associated with a lack of or need for, nitric oxide (NO) by increasing NO concentration comprising administering to a human in need thereof a compound of formula (I)

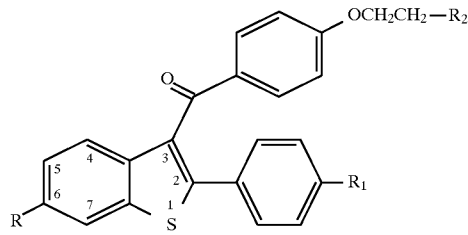

Wherein:

R is hydrogen, —OH, —O($C_1$–$C_4$ alkyl), —OCO($C_1$–$C_4$ alkyl), or —OCOAr where Ar is a phenyl or optionally substituted phenyl;

$R_1$ is R, —Cl, or —F;

$R_2$ is 1-pyrrolidinyl, 1-piperidinyl, or 1-hexamethyleneimino;

or a pharmaceutically acceptable salt or solvate thereof.

4. A method of according to claim 3 wherein said compound of formula (I) is [2-(4-hydroxyphenyl)-6-hydroxybenzo[b]thien-3-yl][4-[2-(1-piperidinyl)ethoxy]phenyl]methanone hydrochloride.

* * * * *